United States Patent
Chin et al.

(10) Patent No.: US 11,571,190 B2
(45) Date of Patent: *Feb. 7, 2023

(54) METHODS AND DEVICES FOR FALLOPIAN TUBE DIAGNOSTICS

(71) Applicant: Boston Scientific Scimed, Inc., Maple Grove, MN (US)

(72) Inventors: Albert Chin, Palo Alto, CA (US); Surbhi Sarna, San Francisco, CA (US); David W. Snow, Saratoga, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 249 days.

This patent is subject to a terminal disclaimer.

(21) Appl. No.: 16/834,507

(22) Filed: Mar. 30, 2020

(65) Prior Publication Data
US 2020/0245983 A1 Aug. 6, 2020

Related U.S. Application Data

(63) Continuation of application No. 14/764,710, filed as application No. PCT/US2014/014472 on Feb. 3, 2014, now Pat. No. 10,646,209.
(Continued)

(51) Int. Cl.
*A61B 10/04* (2006.01)
*A61B 10/02* (2006.01)
(Continued)

(52) U.S. Cl.
CPC .......... *A61B 10/04* (2013.01); *A61B 1/00082* (2013.01); *A61B 1/00101* (2013.01);
(Continued)

(58) Field of Classification Search
None
See application file for complete search history.

(56) References Cited

U.S. PATENT DOCUMENTS

| 3,881,464 A | 5/1975 | Levene |
| 4,324,262 A | 4/1982 | Hall |

(Continued)

FOREIGN PATENT DOCUMENTS

| CN | 101257943 A | 9/2008 |
| CN | 101869491 A | 10/2010 |

(Continued)

*Primary Examiner* — Sean P Dougherty
*Assistant Examiner* — Benjamin S Melhus
(74) *Attorney, Agent, or Firm* — Seager, Tufte & Wickhem, LLP

(57) ABSTRACT

Methods and devices for performing minimally invasive procedures useful for Fallopian tube diagnostics are disclosed. In at least one embodiment, the proximal os of the Fallopian tube is accessed via an intrauterine approach; an introducer catheter is advanced to cannulate and form a fluid tight seal with the proximal os of the Fallopian tube; a second catheter inside the introducer catheter is provided to track the length of the Fallopian tube and out into the abdominal cavity; a balloon at the end of the second catheter is inflated and the second catheter is retracted until the balloon seals the distal os of the Fallopian tube; irrigation is performed substantially over the length of the Fallopian tube; and the irrigation fluid is recovered for cytology or cell analysis.

20 Claims, 21 Drawing Sheets

Related U.S. Application Data

(60) Provisional application No. 61/873,753, filed on Sep. 4, 2013, provisional application No. 61/759,783, filed on Feb. 1, 2013.

(51) Int. Cl.

| | | |
|---|---|---|
| *A61B 1/303* | (2006.01) | |
| *A61M 25/00* | (2006.01) | |
| *A61M 25/10* | (2013.01) | |
| *A61B 90/00* | (2016.01) | |
| *A61B 1/00* | (2006.01) | |
| *A61B 17/12* | (2006.01) | |
| *A61B 17/00* | (2006.01) | |
| *A61M 25/04* | (2006.01) | |
| *A61B 17/42* | (2006.01) | |
| *A61B 17/34* | (2006.01) | |

(52) U.S. Cl.
CPC .......... *A61B 1/303* (2013.01); *A61B 10/0291* (2013.01); *A61B 17/12045* (2013.01); *A61B 17/12136* (2013.01); *A61B 90/39* (2016.02); *A61M 25/0082* (2013.01); *A61M 25/1002* (2013.01); *A61M 25/10181* (2013.11); *A61B 2010/0216* (2013.01); *A61B 2017/00004* (2013.01); *A61B 2017/00557* (2013.01); *A61B 2017/00893* (2013.01); *A61B 2017/3435* (2013.01); *A61B 2017/4233* (2013.01); *A61B 2090/3904* (2016.02); *A61B 2217/005* (2013.01); *A61B 2217/007* (2013.01); *A61M 25/04* (2013.01); *A61M 2025/0096* (2013.01); *A61M 2025/105* (2013.01); *A61M 2025/109* (2013.01); *A61M 2025/1065* (2013.01); *A61M 2210/1425* (2013.01)

(56) References Cited

U.S. PATENT DOCUMENTS

| | | | |
|---|---|---|---|
| 5,389,089 | A | 2/1995 | Bauer et al. |
| 5,630,797 | A * | 5/1997 | Diedrich ............ A61M 25/0119 604/533 |
| 2008/0097469 | A1 | 4/2008 | Gruber et al. |
| 2014/0088459 | A1* | 3/2014 | Roush ................... A61B 10/04 600/569 |
| 2014/0171828 | A1* | 6/2014 | Blitzer ........... A61B 17/320725 600/570 |

FOREIGN PATENT DOCUMENTS

| | | |
|---|---|---|
| JP | 55032576 A | 3/1980 |
| JP | S5532576 A | 3/1980 |
| JP | H03277374 A | 12/1991 |
| JP | H05200120 A | 8/1993 |
| JP | 08071155 A | 3/1996 |
| JP | H08299287 A | 11/1996 |
| JP | 2000135197 A | 5/2000 |
| JP | 2006511271 A | 4/2006 |
| JP | 2009540928 A | 11/2009 |
| JP | 2010533513 A | 10/2010 |
| JP | 2015173692 A | 10/2015 |

\* cited by examiner

PROTOTYPE EVERTING BALLOON WITH OUTER CONSTRICTION SLEEVE

1. INFLATE/EVERT ELASTIC BALLOON; INELASTIC SLEEVE CONSTRICTS PREDMAL BALLOON LENGTH

2. FULLY EVERTED DIGITAL BALLOON TIP EXPANDS (3-1 BALLOON TO SLEEVE DIAMETER)

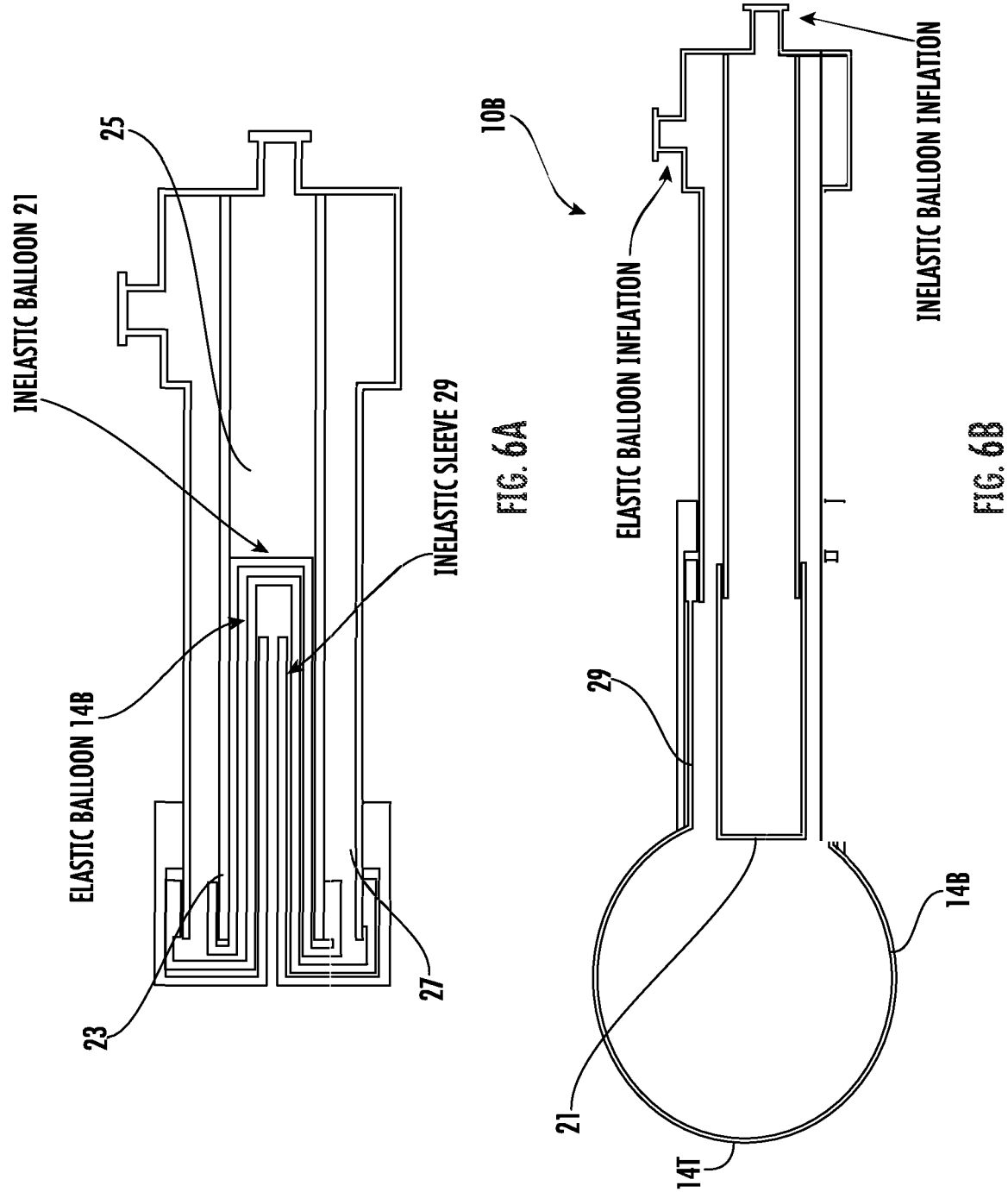

METHODS AND DEVICES FOR FALLOPIAN TUBE DIAGNOSTICS

RELATED APPLICATIONS

This application is a continuation of U.S. application Ser. No. 14/764,710, filed Jul. 30, 2015, which is a 371 U.S. National Stage of PCT Application No. PCT/US14/14472, filed Feb. 3, 2014, which claims priority benefit of U.S. Provisional Application Ser. No. 61/873,753 filed Sep. 4, 2013, and U.S. Provisional Application Ser. No. 61/759,783 filed Feb. 1, 2013, the disclosures of which are herein incorporated herein by reference in their entirety.

FIELD OF THE INVENTION

The present invention in general relates to Fallopian tube diagnostics and in particular to a catheter that accommodates the anatomical difficulties associated with navigation within the Fallopian tube.

BACKGROUND OF THE INVENTION

Ovarian cancer is a significant disease in women; 1 out of 72 women in the U.S. is diagnosed with ovarian cancer sometime during her lifetime. In 2012, 22,280 women in the U.S. were diagnosed with this illness, and 15,500 women died of this malignancy.

Definitive detection of ovarian cancer presently requires a surgical procedure to obtain cell samples for diagnosis. Since the ovaries are intra-abdominal, laparoscopic or open surgery (laparotomy) must be performed to access the ovaries for evaluation. Furthermore, biopsy of the ovary is not generally recommended by medical guidelines as there exists a risk of spreading the cancer further.

Anatomically, the ovaries are in close proximity of the fimbria at the region of the distal opening or os of the Fallopian tube. Eggs released by the ovary are gathered by the fimbria and transported through the Fallopian tube to the uterus. In ovarian cancer, cells may be deposited in the Fallopian tube; a few of these cells may find their way into the uterus. Cell samples obtained from the uterus may detect ovarian malignancy; however, the incidence of retrograde migration of ovarian cancer cells into the uterus is too low to render uterine sampling a reliable diagnostic test for ovarian malignancy. A higher number of ovarian cancer cells migrate to the Fallopian tube; this number increases in the distal portion of the tube, near the distal os. The ability to test cells in the Fallopian tube for malignancy would be of considerable clinical value for the early detection and treatment of such cancers, if such could be performed without concern about spreading cancerous cells.

Thus, there exists a need for a device and process to allow cell samples to be obtained from Fallopian tube for evaluation of ovarian cancer in a minimally invasively fashion and, particularly without the need for a skin incision. There further exists a need for securing a sample of representative cells from the Fallopian tube with a catheter to screen for early stage cancers.

SUMMARY OF THE INVENTION

Methods and devices for performing minimally invasive procedures useful for Fallopian tube diagnostics are disclosed. In at least one embodiment, the proximal os of the Fallopian tube is accessed via an intrauterine approach; an introducer catheter is advanced to cannulate and form a fluid tight seal with the proximal os of the Fallopian tube; a second catheter inside the introducer catheter is provided to track the length of the Fallopian tube and out into the abdominal cavity; a balloon at the end of the second catheter is inflated and the second catheter is retracted until the balloon seals the distal os of the Fallopian tube; irrigation is performed substantially over the length of the Fallopian tube; and the irrigation fluid is recovered for cytology or cell analysis.

BRIEF DESCRIPTION OF THE DRAWINGS

The present invention is further detailed with respect to the following non-limiting specific embodiments of the present invention. The appended claims should not be construed as being limited to the specific devices so detailed.

FIGS. 6A and 6B are schematic, cross-sectional views of an everting (sleeve and elastic balloon) with an inelastic delivery balloon in a deflated state (A); and an inflated state (B);

DESCRIPTION OF THE INVENTION

Figures 1A, 1B, 1C, 1D:
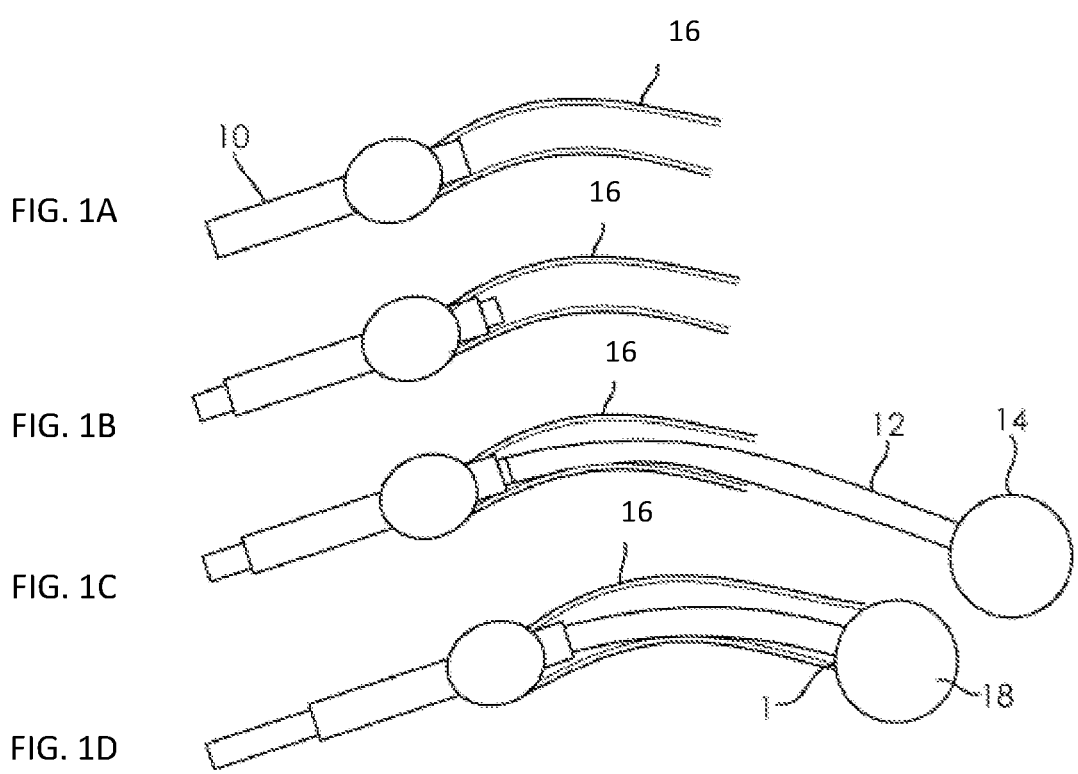
FIGS. 1A-1D are schematic, cross-sectional side views that depict the sequential insertion of a specific embodiment of an invention catheter into a Fallopian tube insertion catheter to seal against a Fallopian tube end (A); an everting sleeve catheter is inserted through insertion catheter into the tube (B); a distal balloon is inflated as the sleeve is extended (C); and (D) irrigation is deployed to remove cells from the Fallopian tube lumen wall.

The present invention has utility in engaging the interior wall of the Fallopian tube and effectively removing cells therefrom for diagnostic purposes. A device and process is provided for collecting such cells in a minimally invasive procedure that in some embodiments occurs without cutaneous incision.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It must be noted that as used herein and in the appended claims, the singular forms "a", "an", and "the" include plural referents unless the context clearly dictates otherwise. Thus, for example, reference to "a balloon" includes a plurality of such balloons and reference to "the channel" includes reference to one or more channels and equivalents thereof known to those skilled in the art, and so forth.

Embodiments of an inventive catheter for Fallopian tube diagnostics are provided for the performance of minimally invasive procedures including (1) Access to the proximal os of the Fallopian tube via an intrauterine approach; (2) Advance of an introducer catheter to cannulate and form a fluid tight seal with the proximal os; (3) Use of a second catheter inside the introducer catheter to track the length of the Fallopian tube and out into the abdominal cavity; (4) Inflation of a balloon at the end of the second catheter with retraction of the second catheter until the balloon seals the distal os of the Fallopian tube. Retraction of the second catheter produces contact with the intraluminal surface of the Fallopian tube to dislodge cells for improved sampling; and (5) and provisions to irrigate the Fallopian tube and recover the irrigation fluid for cytology or cell analysis.

Typically, it is very difficult to pass a catheter through the Fallopian tube. The Fallopian tube is curved, and the soft tissue of the tube collapses, resulting in multiple constrictions as passage is attempted. In at least one embodiment of the present invention, an elongated balloon that is initially inverted into a catheter lumen is deployed. The balloon everts upon pressurization inside the catheter, and the unrolling mechanism of the eversion creates a path through the Fallopian tube, regardless of tortuosity or constriction in the Fallopian tube. The great majority of the length of the balloon should be substantially inelastic, such that the balloon does not substantially expand and dilate the Fallopian tube as it everts, preferably so the Fallopian tube does not expand or dilate as the balloon everts. Balloon expansion may burst or injure the Fallopian tube. However, the design also incorporates an elastic distal balloon end that expands to allow sealing of the distal os upon balloon retraction.

An inventive process common to the various embodiments of inventive devices includes the deployment of the distal end of a catheter. In some inventive embodiments, an inventive catheter distal end is delivered to a proximal end of the Fallopian tube with resort to a conventional hysteroscope. Regardless of the mode of deployment, a retracted portion of an inventive catheter is extended into contact with the interior wall of the Fallopian tube. It has been surprisingly found that the act of extending the portion abrades sufficient cells from the Fallopian tube wall to perform histological evaluation. This is observed for planar surfaces of seemingly non-abrasive character. While an abrasive is present on the tube contacting surfaces in some embodiments, such an abrasive is found not to be necessary. It has also been surprisingly found that withdrawal of the extended portion removes still more cells. In other inventive processes the extended portion is retracted prior to catheter removal so as to preclude dispersal of dislodged Fallopian tube cells to surrounding tissue. Upon catheter removal contacting the exposed portion, now covered in cells with a microscope slide or other diagnostic substrate, is sufficient to test for abnormal cells and in particular cancerous cells.

Referring now to the figures, in FIGS. 1A-1D an introduction catheter 10 with an inverted inelastic sleeve 12 and an attached distal elastic balloon 14 is (A) inserted through an introduction catheter 10 that resides in the working channel 22 of an operative hysteroscope 20 (FIG. 2), and used to cannulate the proximal os of the Fallopian tube 16; (B) inflated to evert the sleeve 12 the length of the Fallopian tube 16 and distend the distal elastic balloon 14; and (C) retracted slightly to seal the distal os 18 of the Fallopian tube 16 with the inflation of the elastic balloon 14 upon full advancement of the inverted elastic sleeve 12. FIG. 1D illustrates the introduction of saline to irrigate the length of the Fallopian tube 16 between the introducer catheter 10 and the everted sleeve 12 with the retraction of the inflated elastic balloon 14 that seals the opening of the distal os, and the subsequent collection of the irrigation fluid to obtain cell samples from substantially the entire length of the Fallopian tube for cell analysis in the detection of ovarian cancer or other medical condition in FIG. 1D.

Figure 2:
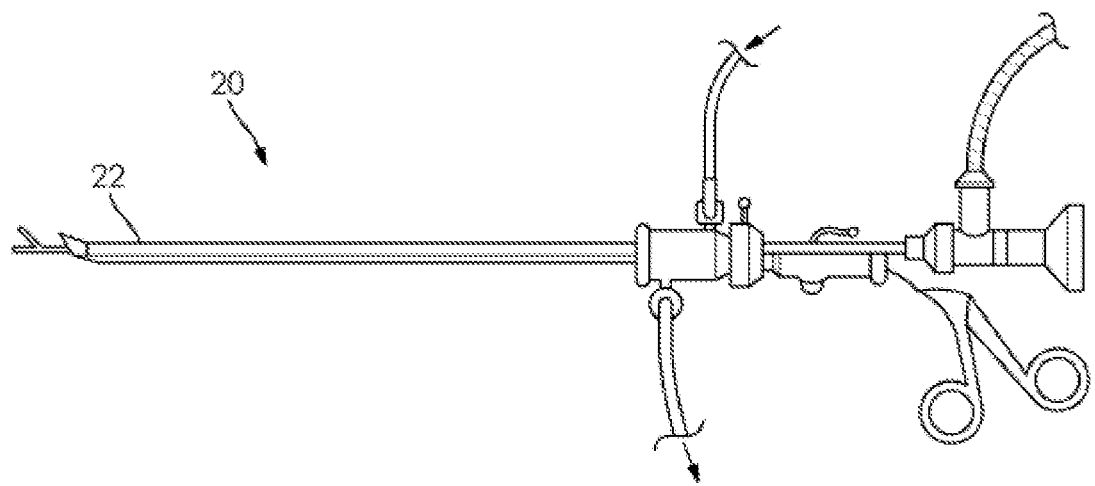
FIG. 2 is a schematic of a hysteroscope suitable for deploying the catheters of FIGS. 1A-1D.
Figure 3:
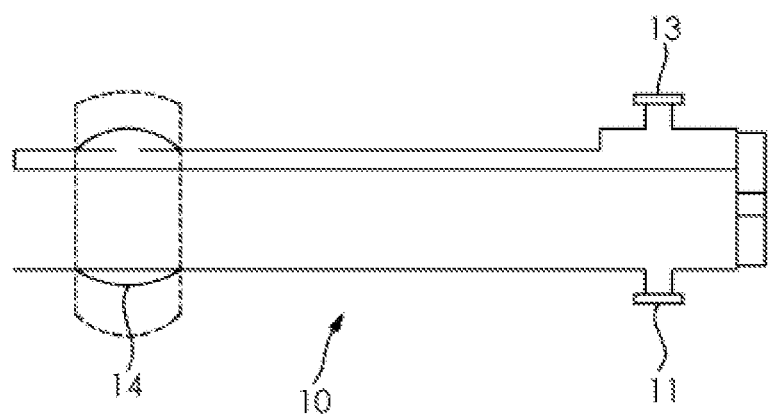
FIG. 3 is a schematic view of an embodiment of a proximal introducer catheter.

The catheter 10 described above, and in greater detail below may be introduced into the uterus of a patient using an operating hysteroscope 20, an example of which is shown in FIG. 2. An operating hysteroscope contains an endoscope and multiple channels; one channel may provide irrigation to distend the uterus and allow endoscopic visualization, and one or more additional channels 22 may allow instruments and/or catheters to be advanced distal to the hysteroscope. A Proximal Introducer Catheter 10 (see FIG. 1A and FIG. 3) may be advanced through the working channel of the operating hysteroscope, and used to cannulate the proximal os of a Fallopian tube. The balloon 14 on the proximal introducer catheter 10 is inflated to occlude the proximal os, and the everting balloon catheter is advanced through the proximal introducer catheter 10 into the proximal portion of the Fallopian tube. The sleeve/balloon element 14 is fully everted, and the inflated balloon tip pulled back to seal the distal os. Irrigation may be introduced via a port 11, and aspirated via the irrigation port 11 on the proximal introducer catheter 10, to collect the sample. Irrigation may also be introduced through both the everting balloon catheter and the proximal introducer catheter, followed by aspiration through one or both ports (11, 13).

Figure 4A:
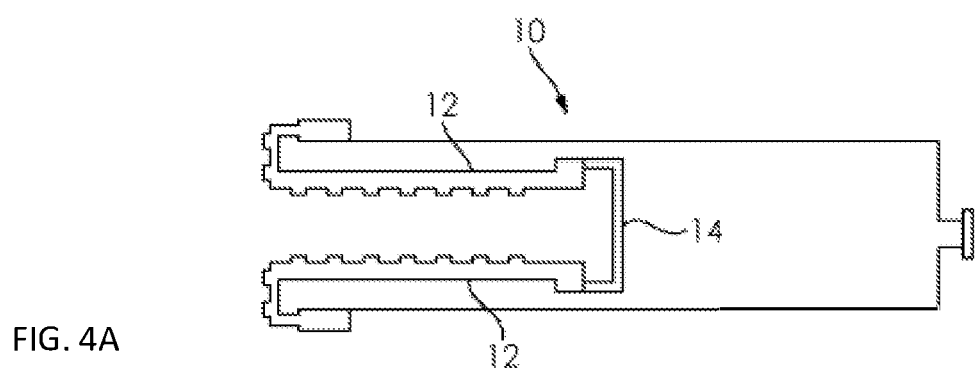
FIGS. 4A and 4B are schematic, cross-sectional views of an everting sleeve with a distal elastic balloon tip in a deflated state (A); and an inflated state (B)
Figure 4B:
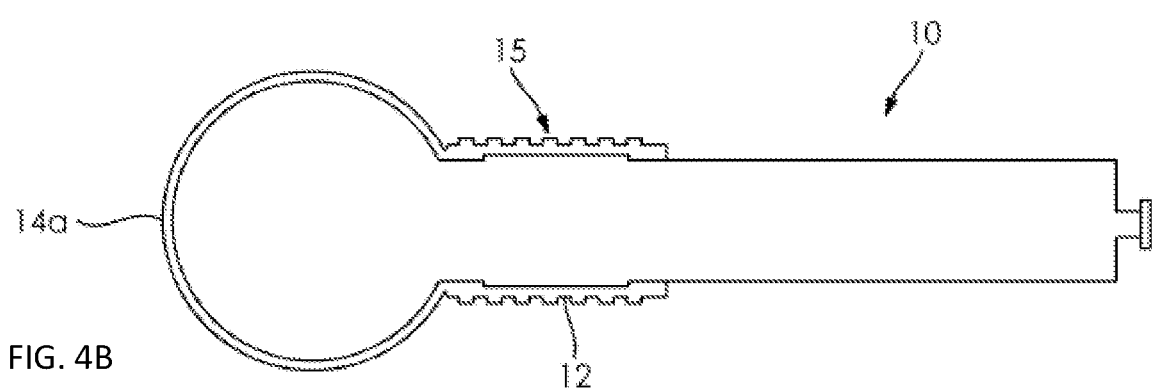

In inventive embodiments of the catheter, the sleeve 12 of the everting sleeve catheter is preferably a flexible, elongated, substantially inelastic tube with an elastic balloon tip 14 attached to its distal end, see FIGS. 4A and 4B. The inelastic tube 12 may have multiple ridges 15 along its length that extend externally of the tube when the tube has been extended/deployed, such as illustrated in FIG. 3B. Prior to deployment, the ridges extend inwardly, as the tube is inverted, as illustrated in FIG. 3A. With the ridges extending externally, as in FIG. 3B, the ridges are exposed to the luminal surface of the Fallopian tube when the sleeve is fully everted. These ridges increase the ability of the sleeve to gather cells upon balloon retraction. Alternatively, the outer surface of the everted inelastic tube may be covered with fabric or otherwise textured, to increase cell dislodgment during balloon retraction.

Figure 5A:
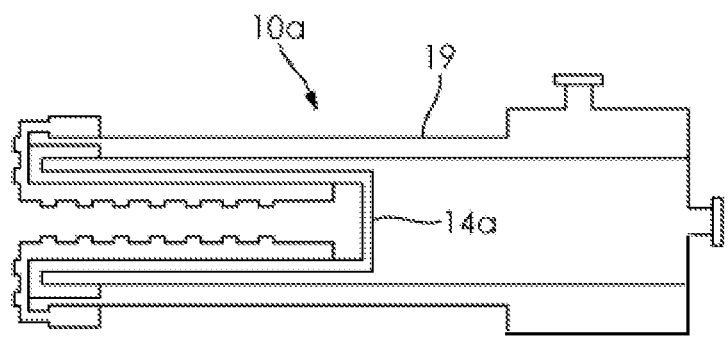
FIGS. 5A and 5B are schematic, cross-sectional views of an everting balloon with an outer construction sleeve in a deflated state (A); and an inflated state (B)
Figure 5B:
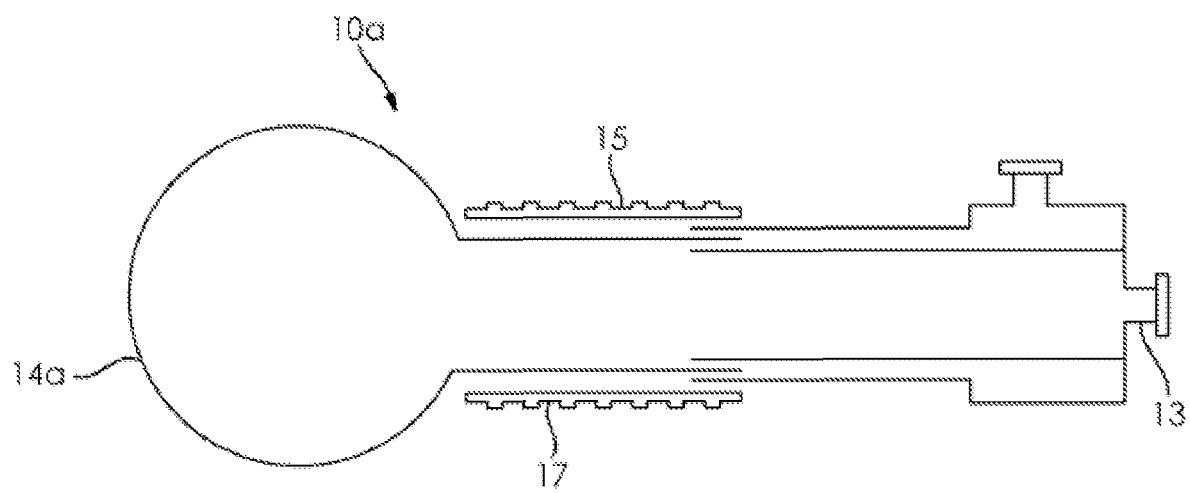
Figure 5C:
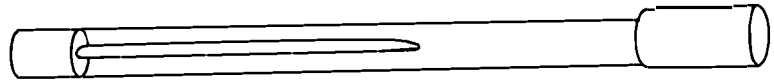
FIG. 5C is a series of photographs of an embodiment of the everting balloon with an outer construction sleeve.
Figure 5C:
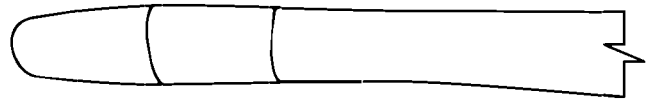
Figure 5C:
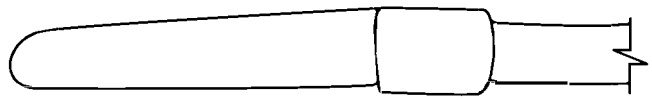
Figure 5C:
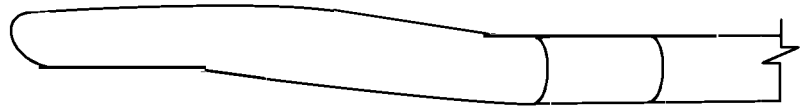
Figure 5C:
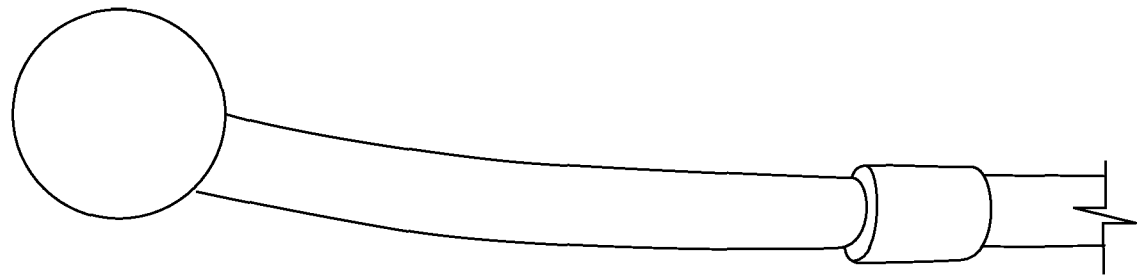

FIGS. 5A-5C illustrate an embodiment of an everting sleeve catheter 10A which provides greater protection of the bond between the balloon and the sleeve of the everting sleeve catheter 10A during deployment, relative to that provided in the embodiment of FIGS. 4A and 4B. The construction of the embodiment of FIGS. 5A-5C involves attachment of an elongated, elastic balloon to the distal tip of the everting sleeve catheter. A substantially inelastic sleeve 17, slightly shorter in length than the elastic balloon 14, is attached to the elastic balloon 14 at the distal tip of the catheter, and inverted so that it lies inside the elastic balloon. Upon eversion of the balloon/sleeve combination 14A, the inelastic sleeve emerges from a double wall 19 of the catheter 10A, and lies on the outside of the elastic balloon and constricts the elastic balloon along the majority of its length, to prevent the elastic balloon from expanding and potentially rupturing the Fallopian tube during the time that the everting sleeve is being advanced through the Fallopian tube. Upon full balloon/sleeve eversion, the distal elastic balloon inflates to $3x$-$5x$ the diameter of the sleeve, for occlusion of the distal os upon retraction of the catheter with concomitant pullback of the inflated balloon. The catheter may contain a port 11 to allow irrigation to occur between the balloon and the outer sleeve, if desired.

Figure 6C:
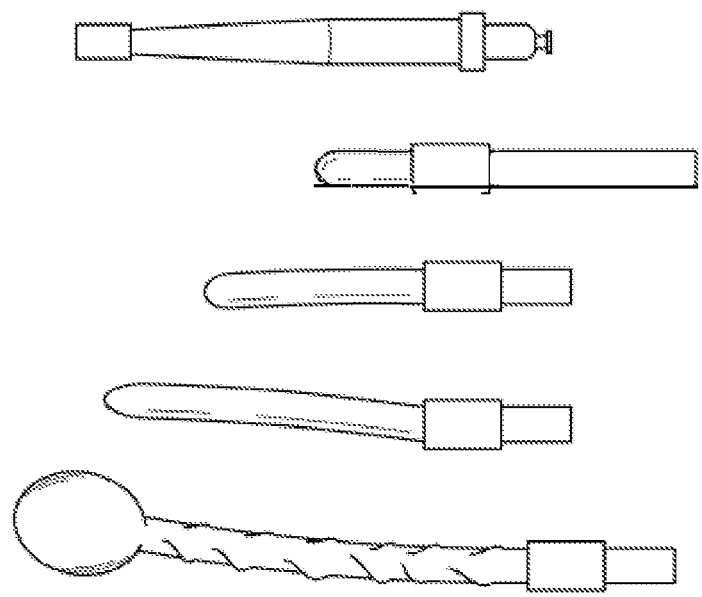
FIG. 6C is a series of photographs of an embodiment of the everting (sleeve and elastic balloon) with an inelastic delivery balloon.

FIGS. 6A-6C illustrate an embodiment of an everting sleeve catheter 10B where a concentric double walled catheter is provided, and the eversion of three layers are attached to the distal catheter tip: (1) an elongated inelastic balloon 21 is attached to the distal tip of the inner catheter 23, and the balloon lies within the inner catheter lumen 25; (2) an elongated elastic balloon 14B equal in length to the inelastic balloon 21 is attached to the distal tip of the outer wall 27 catheter 10B, and it resides inside the inelastic balloon 21; and (3) an inelastic sleeve 29 shorter in length than the elastic balloon 14B is attached to the distal tip of the outer catheter wall 27, and it lies inside the elastic balloon 14B. Pressurization of the inner catheter 23 everts the inelastic balloon 21, which delivers the elastic balloon 14B and outer constricting sleeve 29. Following full eversion of all three layers, pressurization between the walls of the inner catheter and outer catheter inflates the elastic balloon. The inelastic sleeve 29 constricts the elastic balloon 14B along the majority of its length, and the distal, un-constricted tip of the balloon 14T expands to form the occlusion element. The potential advantage of this design is a decrease in frictional characteristics during the eversion process. In this embodiment, the inelastic balloon 21 delivers the elastic balloon and constricting sleeve. The elastic balloon does not undergo expansion until it has been fully everted, and therefore does not increase friction with the wall of an everting sleeve during eversion, as in previous embodiments, which can be a significant advantage in facilitating deployment, particularly when working with small diameter catheters required for traversing the Fallopian tube.

Figure 7A:
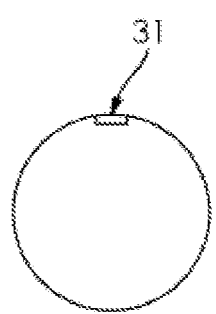
FIGS. 7A and 7B are schematic, cross-sectional views of an everting (sleeve and elastic balloon) with an irrigation lumen in a deflated state (A); and an inflated state (B)
Figure 7A:
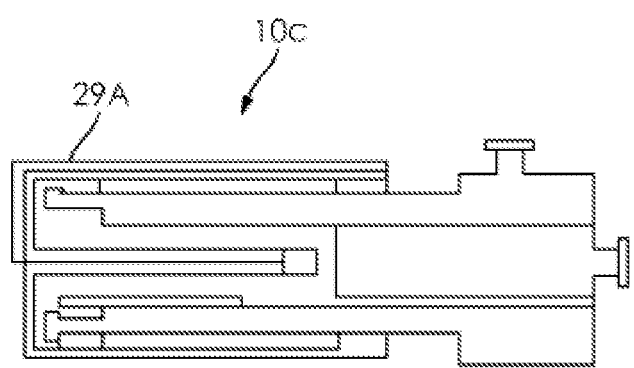
Figure 7B:
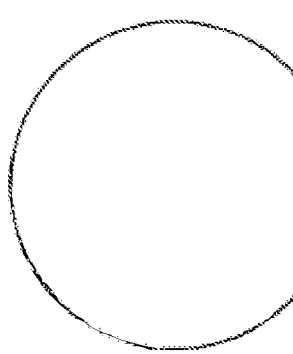
Figure 7B:
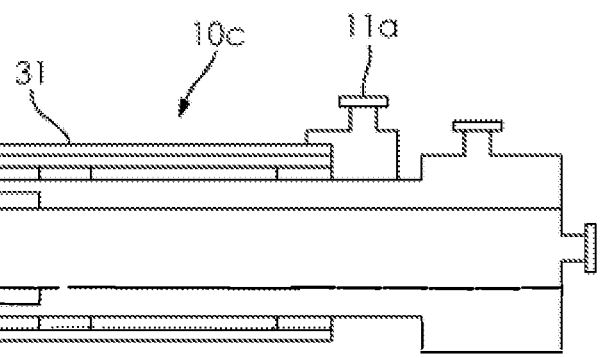
Figure 8A:
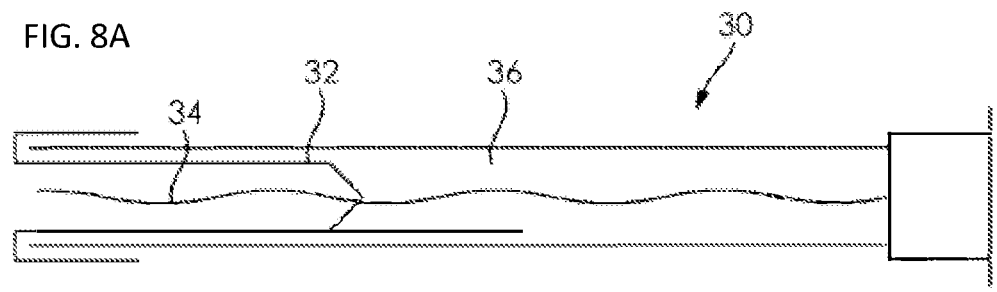
FIGS. 8A and 8B are schematic, cross-sectional views of an everting balloon catheter adapted for placement within an insertion catheter, the everting balloon catheter having a distal filament spiral, where distal is measured relative to the insertion point in a deflated state (A); and an inflated state (B)
Figure 8B:
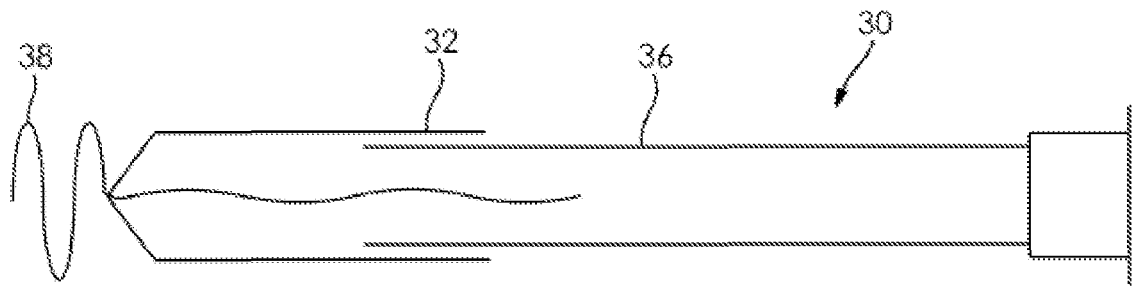
Figure 8C:
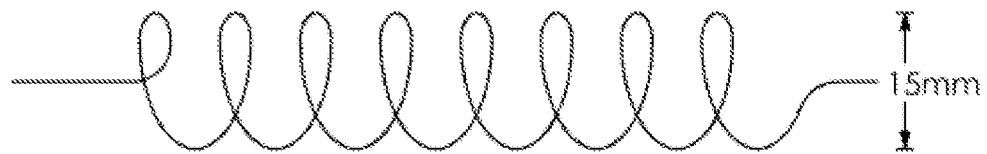
FIG. 8C is a photograph of an exemplary spiral filament with a diameter of 15 millimeters (MM)
Figure 8D:
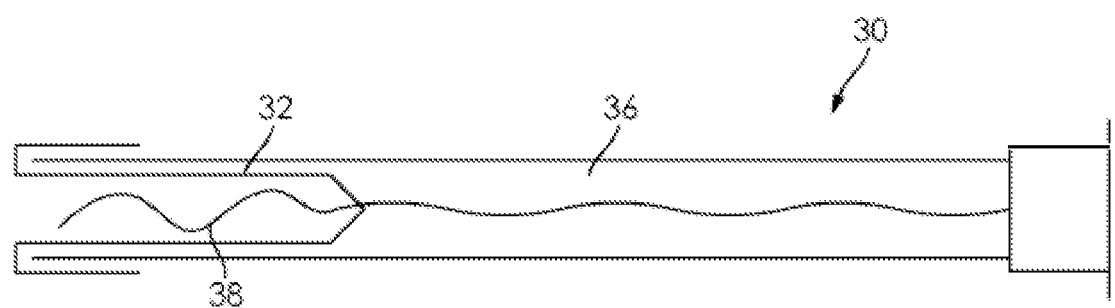
FIGS. 8D and 8E are schematic, cross-sectional views of an everting balloon catheter adapted for placement within an insertion catheter, the everting balloon catheter having a distal filament spiral heated sealed to the balloon, where distal is measured relative to the insertion point in a deflated state (D); and an inflated state (E)
Figure 8E:
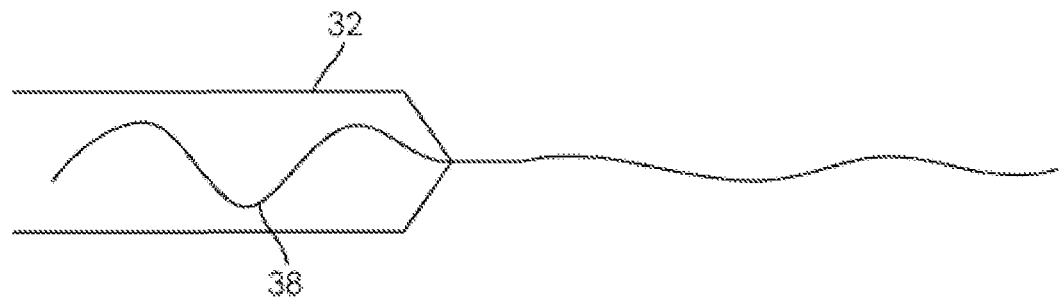
Figure 9:
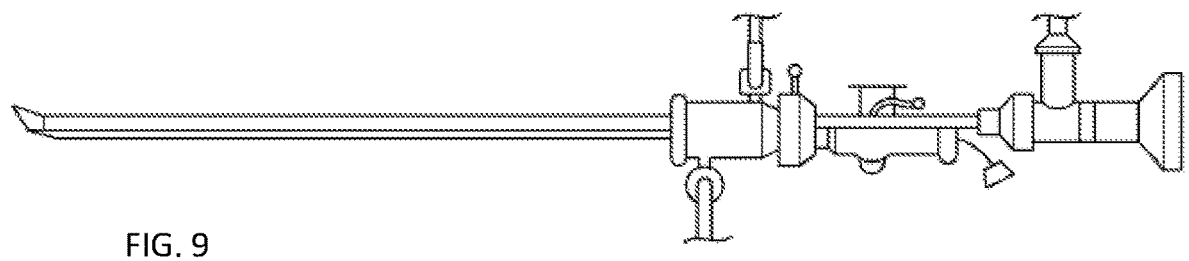
FIG. 9 is a side view of a hysteroscope for deploying the catheters of FIGS. 8A-8E.
Figure 10A:
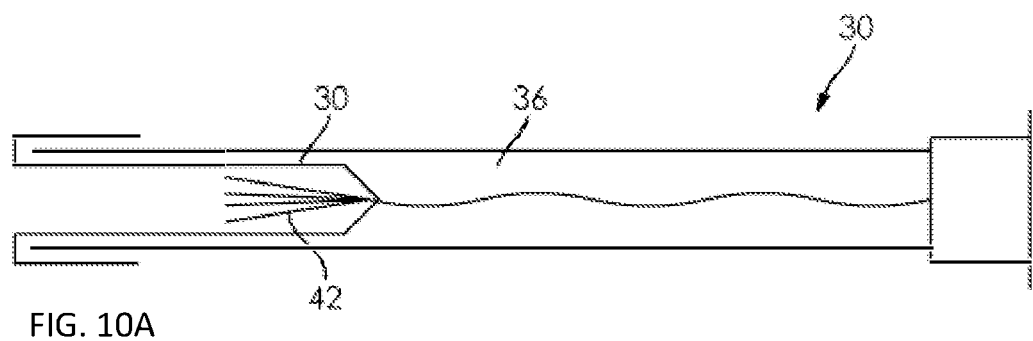
FIGS. 10A and 10B are schematic, cross-sectional views of an everting balloon catheter adapted for placement within an insertion catheter, the everting balloon catheter having a distal expanding brush, where distal is measured relative to the insertion point in a deflated state (A); and an inflated state (B)
Figure 10B:
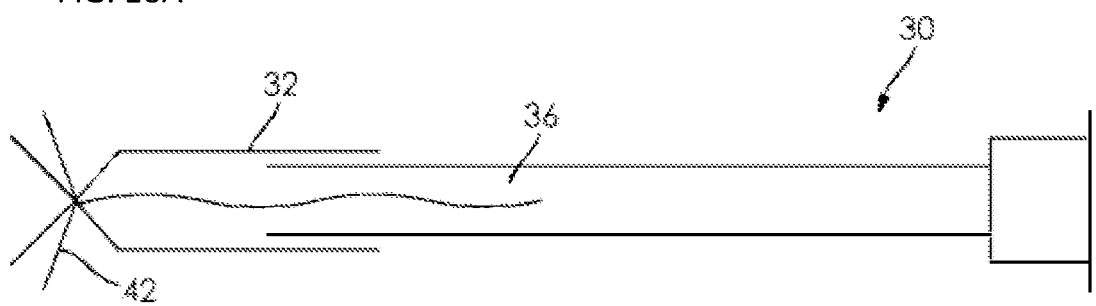

FIGS. 7A and 7B illustrate an embodiment of an everting sleeve catheter 10C with an inelastic sheath 29A that has a small lumen 31 for irrigation, with the lumen 29A connected to a third port 11A used for fluid irrigation and aspiration to obtain cytology samples.

Figure 11A:
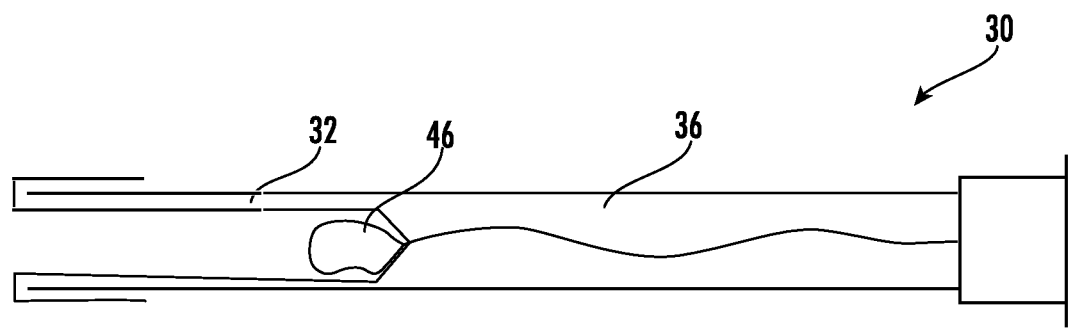
FIGS. 11A and 11B are schematic, cross-sectional views of an everting balloon catheter adapted for placement within an insertion catheter, the everting balloon catheter having a distal expanding foam, where distal is measured relative to the insertion point in a deflated state (A); and an inflated state (B)
Figure 11B:
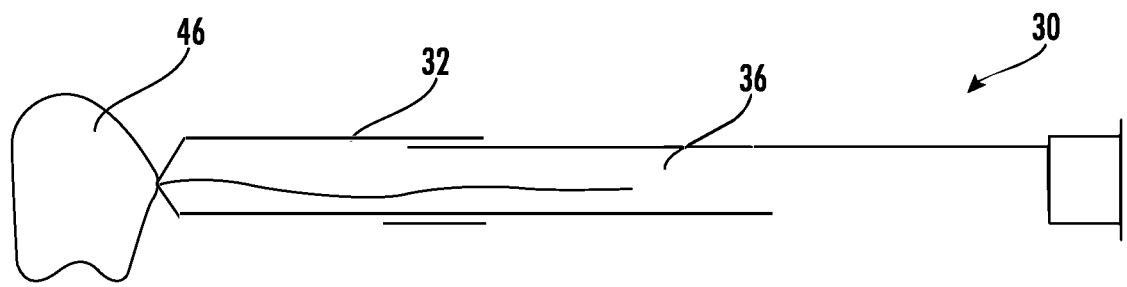

A modified design is shown in FIGS. 8A-8E. An elongated balloon 32 with an expandable member 34 attached to the distal end of the balloon 32 is inverted into the lumen 36 of a catheter 30. Upon inversion, the expandable member 34 lies inside the elongated balloon 32. In certain inventive embodiments, the expandable portion 34 is a spiral of multiple loops 38 of filament. The filament that forms the expandable member 34 is readily formed from a variety of materials illustratively including monofilament plastic material such as Nylon or polypropylene, fluoropolymers, or polylactic acid; metal such as stainless steel titanium, or platinum; or a superelastic metal such as Nitinol. In some embodiments a fiducial marker is present (not shown) to facilitate subsequent return to the situs of cell sampling. It is appreciated that the expanding portion may also have alternative configurations. For example, the expanding portion 34 may contain multiple outwardly oriented bristles 40 of plastic or metal (FIG. 17); or the expanding portion 34 is present as an elongated strand of material that curls 38, spreads or fans out 42, balls up 44 to a predetermined shaped when released from being constrained inside the catheter (FIGS. 10A-10B or FIGS. 13A-13B); or it may be compressed plastic foam that expands upon release into a wet environment (FIGS. 11A-11B). Upon pressurizing the catheter adjacent to the distal os, the balloon 32 everts so as to urge the inverted portion outward into the extended position and into contact with the Fallopian tube inner wall cells. In certain inventive embodiments, upon full balloon eversion, the extending portion 34 is delivered out of the distal os of the Fallopian tube, into the abdominal cavity. The extending portion 34 in some embodiments has to an outer diameter of approximately 15-20 mm.

Figure 17:
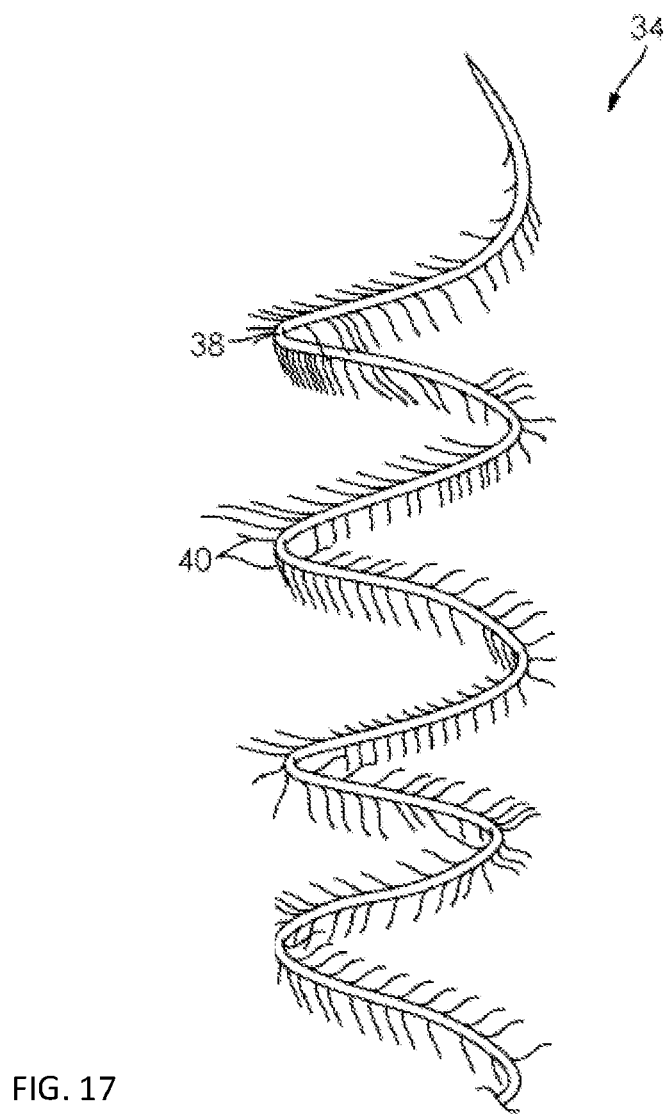
FIG. 17 is a photograph of a platinum coil wire having fibers extending therefrom and operative herein in the context of a catheter as depicted in FIGS. 8A-8E.
Figure 18:
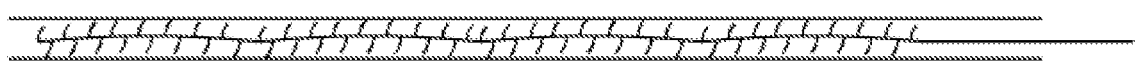
FIG. 18 is an illustration of a separate extending portion with the lumen of the catheter of FIG. 9.
Figure 19:
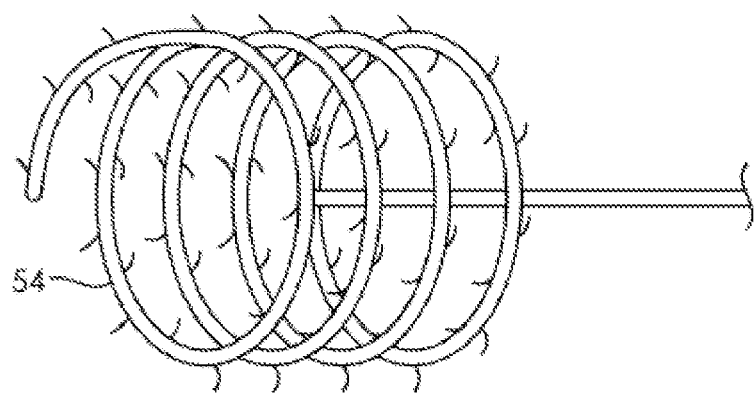
FIG. 19 is an illustration of the separate extending portion in deployed form beyond the orifice in the catheter of FIG. 9.

An advantage of the extending portion 34 having multiple bristles is that there is a lot of surface area on which cells can be collected, including areas that are not likely to be exposed to shear forces when the device is pulled back in. This approach can maximize cell collection and minimize the amount of cells that are wiped off when the device is pulled through the Fallopian tube or into a sheath, as seen in FIGS. 17-19. In those embodiments in which the extending portion has greater surface area, the cell collection typically increases per linear unit of Fallopian tube so engaged under like pressurization conditions, as compared to a contourless extending portion.

Figure 12A:
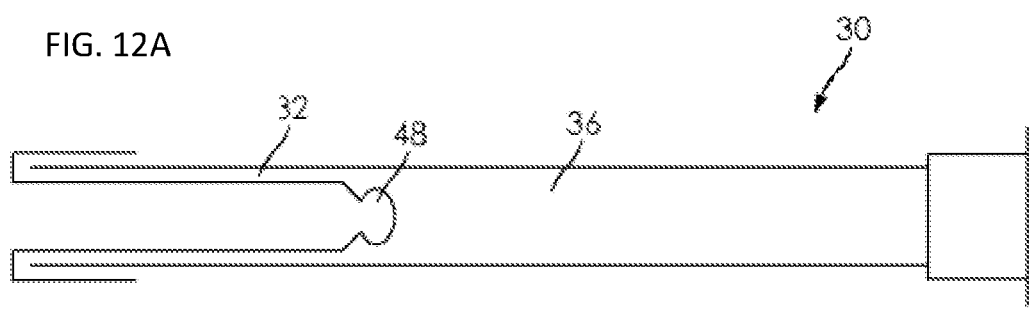
FIGS. 12A and 12B are schematic, cross-sectional views of an everting balloon catheter adapted for placement within an insertion catheter, the everting balloon catheter having a distal expanding inflated spherical balloon appendage, where distal is measured relative to the insertion point in a deflated state (A); and an inflated state (B)
Figure 12B:
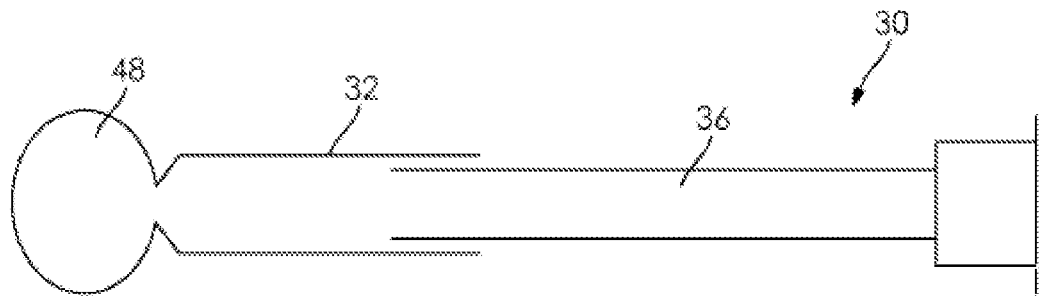
Figure 13A:
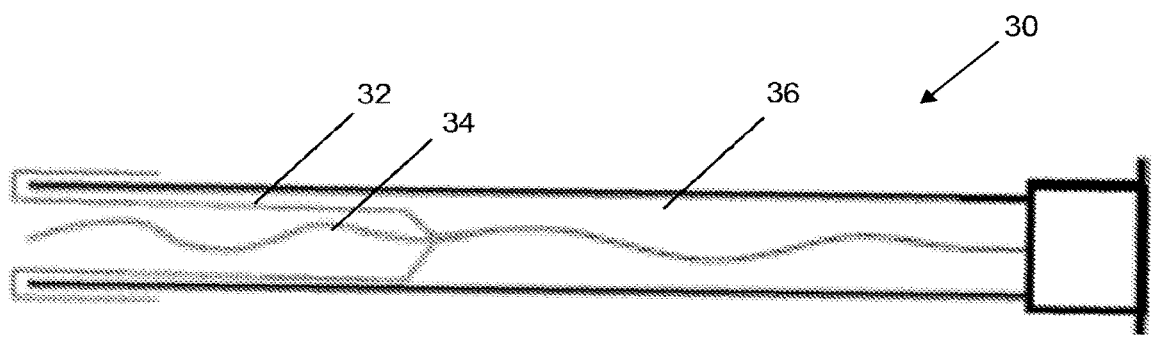
FIGS. 13A and 13B are schematic, cross-sectional views of an everting balloon catheter adapted for placement within an insertion catheter, the everting balloon catheter having a distal superelastic coil, where distal is measured relative to the insertion point in a deflated state (A); and an inflated state (B)
Figure 13B:
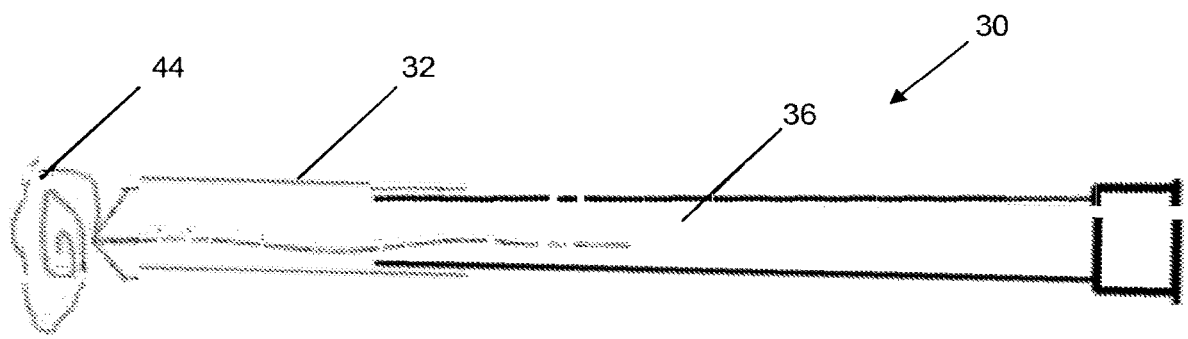
Figure 14A:
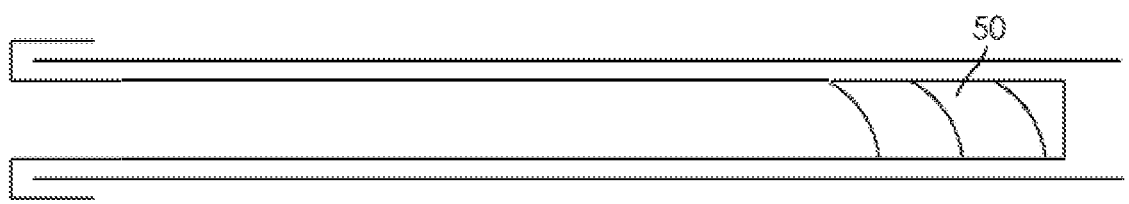
FIGS. 14A and 14B are schematic, cross-sectional views of an everting balloon spiral cannula adapted for placement within an insertion catheter, the cannula having a distal expanding inflated spiral balloon appendage, where distal is measured relative to the insertion point in a deflated state (A); and an inflated state (B)
Figure 14B:
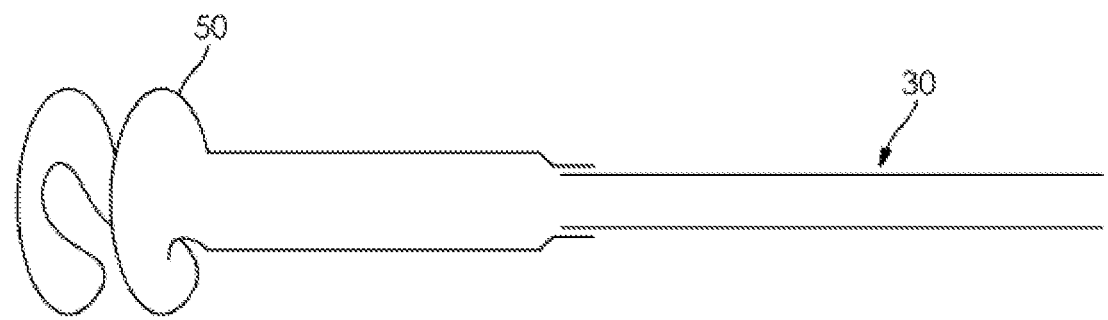
Figure 15A:
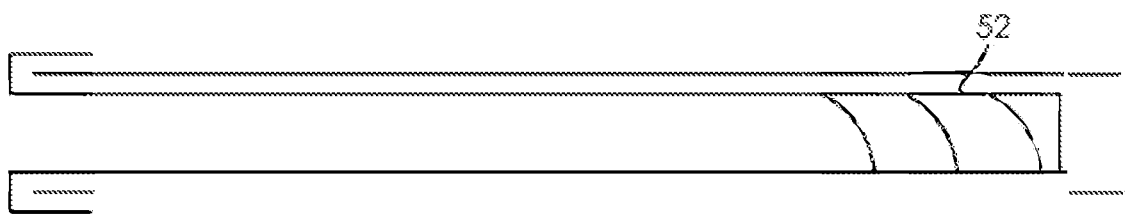
FIGS. 15A and 15B are schematic, cross-sectional views of an everting distal arc balloon cannula adapted for placement within an insertion catheter, where distal is measured relative to the insertion point in a deflated state (A); and an inflated state (B)
Figure 15B:
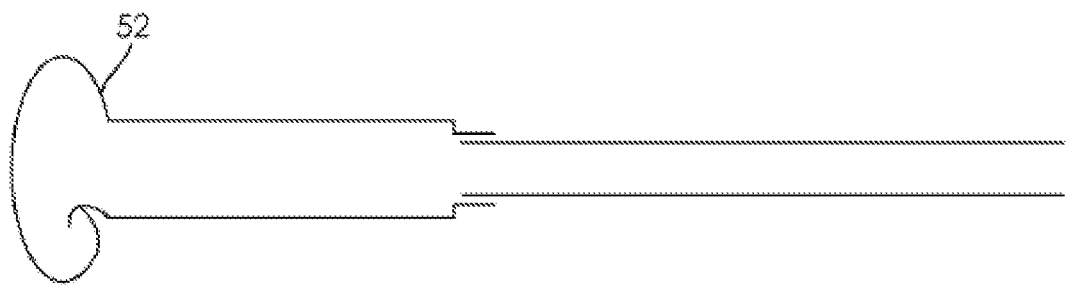

In still other embodiments of an inventive catheter, the extending portion, upon deployment defines: multiple filaments 42 attached to the distal end of the balloon 32 that splay out upon balloon eversion to form a brush 42 (FIGS. 10A-10B); a plastic foam structure 46 that is compressed inside the balloon 32 and expands on balloon 32 eversion and exposure to a fluid environment (FIGS. 11A-11B); an elastic or inelastic balloon 48 on the distal end of the inelastic sleeve balloon 32 (FIGS. 12A-12B), an everting balloon with a superelastic wire coil (FIGS. 13A-13B), a spiral everting balloon 50 (FIGS. 14A-14B), an everting distal arc balloon 52 FIGS. 15A-15B); or a long elastic filament of plastic or metal that gathers into a three-dimensional structure upon balloon eversion, such as an inner lumen 54 (FIGS. 16A-16B), and expanding portion 34 with multiple outwardly oriented bristles 40 (FIG. 17). It is appreciated that any of these embodiments of an inventive catheter extending portion are readily fitting with a fiducial marker that can be used to navigate back to the Fallopian tube as needed. Such markers are known to the art and illustratively include radio-opacity markers, isotopic markers, and radiofrequency markers. In still other embodiments, a biodegradable extending portion or a permanent extending portion are severed from the catheter. In still other embodiments, the extending portion delivers a therapeutic agent such as a chemotherapeutic drug, antibiotic, anti-inflammatory, or combinations thereof of the Fallopian tube tissue.

When the catheter is pulled into the working channel of the hysteroscope, cells are dislodged from the entire length of the inner surface of the Fallopian tube. In some embodiments, the extending portion is inverted through reduced gas pressure with the balloon so as to shield collected cells with the catheter tip region internal bore (FIG. 18).

Without intending to be bound by a particular theory, the expanding portion creates friction between the outer surface of the expanding portion and the inner lining of the Fallopian tube sufficient to dislodge cells and adhere such cells to the expanding portion, even in certain instances on a contourless expanding portion. The expanded spiral at the distal end of the balloon contacts the fimbria at the distal end of the Fallopian tube, gathering cell samples as it is withdrawn. Since the Fallopian tube increases in inner diameter as it proceeds from its proximal to its distal end, the expanding portion ensures that cell samples are obtained at the distal end of the tube (fimbrial portion of the Fallopian tube). The elongated balloon and the distal expanding portion are in certain procedural embodiments retracted into the working channel of the hysteroscope, to avoid loss of cell samples as the hysteroscope is removed from the patient. An elastomer seal at the proximal end of the working channel of the hysteroscope seals against the outer surface of the catheter. A mark on the catheter body indicates the length of retraction necessary to ensure that the elongated balloon and distal spiral lay within the hysteroscope working channel. Upon removal of the hysteroscope from the patient, in some embodiments, a syringe containing saline solution is attached to the Luer fitting at the proximal end of the working channel, and the saline is used to flush cells gathered by the elongated balloon and expanding spiral into a test tube. It is appreciated that the cells decorating the extending portion are readily collected for testing by conventional techniques and are prepared for cytological, molecular or genetic examination.

Figure 16A:
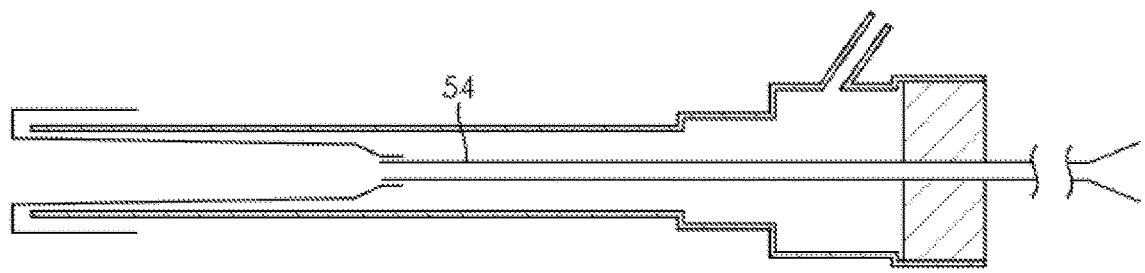
FIGS. 16A and 16B are schematic, cross-sectional views of an everting balloon catheter adapted for placement within an insertion catheter, the everting balloon catheter having a inner lumen that is pressuring to evert, where distal is measured relative to the insertion point in a deflated state (A); and an inflated state (B)
Figure 16B:
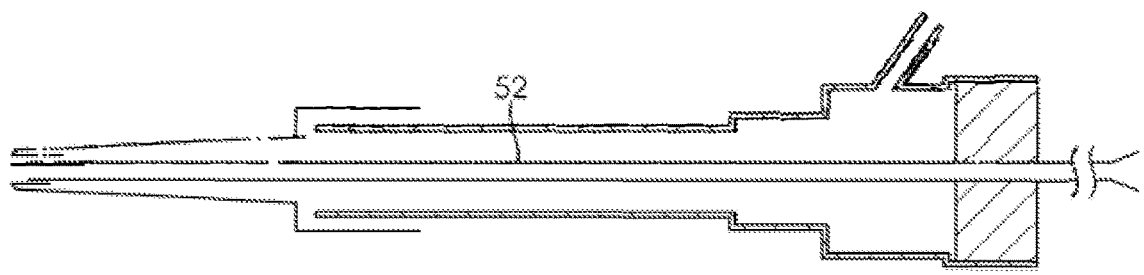

An alternative embodiment of that shown in FIGS. 16A-16B in which a coil is attached to the end of the inverting balloon, an inner lumen formed of the exemplary material polyethylene terephthalate (PET) is attached. The eversion process follows that of the aforementioned embodiments. This alternative embodiment also includes an inflation sideport and a proximal seal that allow the balloon to be inverted while maintaining an orifice through the inner lumen in fluid communication between the hysteroscope and the patient body tissue. Once everted, the inner lumen provides a pathway through which a separate extending portion is passed or a surgical instrument package is passed. An example of such a collection device is the spiral shown in FIG. 18 and FIG. 19. It is appreciated that cells can be collected from a specific portion of the Fallopian tubes, for example the fimbria, and then pulled back into the inner lumen so as to avoid the potential for distal cells to be wiped off by the inner surface of the proximal Fallopian tube as the device is removed.

Any patents or publications mentioned in this specification are herein incorporated by reference to the same extent as if each individual publication was specifically and individually indicated to be incorporated by reference. The foregoing description is illustrative of particular embodiments of the invention, but is not meant to be a limitation upon the practice thereof.

The invention claimed is:
1. A catheter comprising:
  a tube having a distal end;
  a balloon having a distal end secured to the distal end of the tube at a proximal end of the balloon, the balloon having a length, said balloon being adapted to evert from an inverted position to a longitudinally extended everted position in a Fallopian tube, wherein at least a majority of the length of the balloon is inelastic, such that in response to moving between the first inverted position and the second everted position, over-expansion of the Fallopian tube by the balloon is preventable; and
  an extending portion comprising a filament disposed at the distal end of said balloon moveable between the inverted position and the longitudinally extended everted position with eversion of said balloon;
  wherein each of said balloon and said filament has an outer surface configured to collect and retain cells from a wall of the Fallopian tube.

2. The catheter of claim 1, further comprising a pressurized fluid source in selective communication with said balloon.

3. The catheter of claim 1, further comprising a hysteroscope.

4. The catheter of claim 1, wherein said outer surface of the filament is smooth.

5. The catheter of claim 1, wherein said outer surface of the filament is bristled.

6. The catheter of claim 1, comprising a plurality of said filaments.

7. The catheter of claim 1, wherein said balloon includes an inner lumen in the everted position, an orifice at the distal end of the balloon in communication with the inner lumen, and said extending portion passes through said tube and said orifice.

8. The catheter of claim 1, wherein said extending portion is biodegradable.

9. The catheter of claim 1, further comprising a fiducial marker.

10. The catheter of claim 1, further comprising a therapeutic agent.

11. A device for Fallopian tube diagnostics, comprising:
a tube having a distal end and positionable relative to a Fallopian tube; and
a balloon having a distal end and coupled to the distal end of the tube at a proximal end of the balloon, wherein the balloon is configured such that when the distal end of the tube is positioned at a proximal os of the fallopian tube, the balloon is movable between a first inverted position and a second everted position such that the balloon extends into the Fallopian tube in the second everted position, wherein at least a portion of a length of the balloon is inelastic, such that in response to moving between the first inverted position and the second everted position, over-expansion of the Fallopian tube by the balloon is preventable; and
a filament disposed at the distal end of the balloon, wherein the filament has a first configuration relative to the balloon in the first inverted position of the balloon, and a second configuration relative to the balloon in the second everted position of the balloon such that the filament is positioned in the Fallopian tube, said filament having an outer surface configured to collect and retain cells from a wall of the Fallopian tube.

12. The device according to claim 11, further comprising a pressurized fluid source in selective communication with said balloon.

13. The device according to claim 11, wherein said outer surface of the filament is smooth.

14. The device according to claim 11, wherein said outer surface of the filament is bristled.

15. The device according to claim 11, wherein the filament is plurality of filaments.

16. The device according to claim 11, wherein at least a majority of the length of the balloon is inelastic.

17. A device for Fallopian tube diagnostics, comprising:
a tube having a distal end and positionable relative to a proximal os of a Fallopian tube; and
an inelastic balloon having a distal end and coupled to the distal end of the tube at a proximal end of the balloon, the balloon being movable between a first inverted position and a second everted position such that the balloon is extendable in the Fallopian tube in the second everted position; and
a filament disposed at the distal end of the balloon, wherein the filament is configured to extend into the Fallopian tube for cell collection when the balloon is extended in the Fallopian tube in the second everted position.

18. The device according to claim 17, wherein said outer surface of the filament is smooth.

19. The device according to claim 17, wherein said outer surface of the filament is bristled.

20. The device according to claim 17, wherein the filament is plurality of filaments.

* * * * *